US012624399B2

(12) United States Patent
Quintela Fandiño

(10) Patent No.: US 12,624,399 B2
(45) Date of Patent: May 12, 2026

(54) P27 SINGLE-NUCLEOTIDE POLYMORPHISM T2871099G AS A PREDICTOR OF THE BENEFIT OF ENDOCRINE THERAPY ALONE OR IN COMBINATION WITH CDK INHIBITORS IN BREAST CANCER

(71) Applicant: FUNDACIÓN DEL SECTOR PÚBLICO ESTATAL CENTRO NACIONAL DE INVESTIGACIONES ONCOLOGICAS CARLOS III (F.S.P. CNIO), Madrid (ES)

(72) Inventor: Miguel Ángel Quintela Fandiño, Madrid (ES)

(73) Assignee: FUNDACIÓN DEL SECTOR PÚBLICO ESTATAL CENTRO, Madrid (ES)

( * ) Notice: Subject to any disclaimer, the term of this patent is extended or adjusted under 35 U.S.C. 154(b) by 434 days.

(21) Appl. No.: 18/262,812

(22) PCT Filed: Jan. 26, 2022

(86) PCT No.: PCT/EP2022/051700
§ 371 (c)(1),
(2) Date: Jul. 25, 2023

(87) PCT Pub. No.: WO2022/161984
PCT Pub. Date: Aug. 4, 2022

(65) Prior Publication Data
US 2024/0102103 A1      Mar. 28, 2024

(30) Foreign Application Priority Data
Jan. 27, 2021      (EP) .................................... 21382061

(51) Int. Cl.
*C12Q 1/68*          (2018.01)
*C12Q 1/6886*        (2018.01)
(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

WO      WO-2007150044 A2 * 12/2007      ........... C12Q 1/6886

OTHER PUBLICATIONS

International search report for PCT/EP2022/051700 mailed on May 23, 2022.
Figueiredo Jane C et al, "Polymorphisms cMyc-N11S and p27-V109G and breast cancer risk and prognosis", BMC Cancer, Biomed Central, London, GB, vol. 7, No. 1, Jun. 14, 2007 (Jun. 14, 2007), p. 99.
Xiang Heping et al., "Association of CDKN1B gene polymorphisms with susceptibility to breast cancer: a meta-analysis", NL Sep. 27, 2013 (Sep. 27, 2013), vol. 40, No. 11, p. 6371-6377.
Schoendorf Thomas et al, "The V109G polymorphism of the p27 gene CDKN1B indicates a worse outcome in node-negative breast cancer patients", Tumor Biology, vol. 25, No. 5-6, 2004, p. 306-312.
Wei Feng et al, "p27 Kip1 V109G Polymorphism and Cancer Risk: A Systematic Review and Meta-Analysis", Cancer Biotherapy & Radiopharmaceuticals, vol. 27, No. 10, Dec. 1, 2012 (Dec. 1, 2012), p. 665-671.
Johansson Harriet et al, "Prognostic impact of genetic variants of and in a randomized trial for endocrine-responsive postmenopausal breast cancer", Apr. 10, 2019 (Apr. 10, 2019), vol. 20, No. 1, p. 19-26.

* cited by examiner

*Primary Examiner* — Juliet C Switzer
(74) *Attorney, Agent, or Firm* — LUCAS & MERCANTI, LLP

(57)          ABSTRACT

The present invention relates to a method of determining the therapy for treating a subject afflicted from breast cancer comprising determining the P27 T2871099G SNP in a sample of said subject and administering only endocrine therapy if the polymorphism is other than T2871099G, and administering endocrine therapy in combination with at least one CDK4/6 inhibitor if the polymorphism is homozygous T2871099G.

10 Claims, 3 Drawing Sheets

Specification includes a Sequence Listing.

P27 SINGLE-NUCLEOTIDE POLYMORPHISM T2871099G AS A PREDICTOR OF THE BENEFIT OF ENDOCRINE THERAPY ALONE OR IN COMBINATION WITH CDK INHIBITORS IN BREAST CANCER

CROSS-REFERENCE TO RELATED APPLICATIONS

This is a 35 U.S.C. 371 National Stage Patent Application of International Application No. PCT/EP2022/051700, filed Jan. 26, 2022, which claims priority to EP application 21382061.6, filed Jan. 27, 2021, each of which is hereby incorporated by reference in its entirety.

FIELD OF THE INVENTION

The present invention relates to a method for determining the therapy for treating a subject afflicted from breast cancer comprising the determination of the P27 T2871099G single-nucleotide polymorphism (SNP). More specifically, the present invention relates to a method to determine the necessity to combine endocrine therapy with CDK4/6 inhibitors, based on P27 T2871099G SNP, since wild-type or heterozygous patients benefit from endocrine therapy, while SNP homozygous patients have less benefit from the endocrine therapy and require the combined therapy with CDK4/6 inhibitors.

BACKGROUND OF THE INVENTION

Advanced hormone-positive breast cancer patients are currently treated with a combination of endocrine therapy and cyclin-dependent kinases (CDKs) inhibitors. Up until 2015, the standard of care for advanced hormone-positive breast cancer was endocrine therapy alone. The former agents have been the cornerstone drug for managing this disease for decades, and actually a percentage of patients experience very prolonged benefit from them. The different therapeutic endocrine therapies achieved approximately a 9-12 months disease control duration.

After 2015 several trials showed that combining hormonal inhibitors with the CDK inhibitors palbociclib, ribociclib or abemaciclib led to a more than 2-fold increase in the disease control duration (more than 20 months in average). This increase was observed in virtually all subgroups, and soon became the new standard of care for advanced hormone-positive breast cancer. Given its widespread benefit, now, all patients are considered candidates for the double blockade in the first line for advanced hormone-positive breast cancer.

However, in early hormone-positive breast cancer, this combination therapy implies two potential problems: 1) pharmaco-economy: the combination treatment costs more than 5,000 Euro per month, whereas endocrine therapy alone costs less than 100 Euro per month; 2) toxicity: the toxicity of endocrine therapy alone is very low and well managed without close and frequent visits to the hospital; CDK inhibitors add considerable toxicity (haematological, gastro-intestinal, asthenia, skin toxicity, etc.) and require frequent visits and tests, associated to a lower quality of life.

No biomarker suggests or pinpoints a subgroup of patients with early hormone-positive breast cancer that could benefit from endocrine therapy alone and obtain a similar benefit to that observed from the combination, albeit at a lower toxicity and monetary cost.

Cyclin Dependent Kinase 4 and 6 (CDK4/6) inhibitors have meant a great advance in metastatic, hormone-positive breast cancer. The addition of palbociclib, ribociclib or abemaciclib to aromatase inhibitors in the first line treatment has increased the progression-free survival time from 10 months (aromatase inhibitor alone) to more than 25 months (aromatase inhibitor plus either CDK4/6 inhibitor). The benefit of these drugs seems to be independent of several factors: being Luminal A, Luminal B or HER2-enriched, patient's age, presence or absence of visceral metastases and others.

In early disease, the situation is quite different: approximately 80-85% of the patients suffering from an early, hormone-positive breast cancer are cured in the long-term, just with surgery and aromatase inhibitors. Recently, three clinical trials have tested the addition of palbociclib (PAL-LAS trial), ribociclib (NATALEE trial) or abemaciclib (monarch-E trial). All trials have accrued approximately 5,000 patients each, and the results are disappointing: the monarch-E trial has reported a 5% improvement in the outcomes (in the 3 years follow up, the ratio disease free survival is 83.4% for endocrine therapy alone and 88.8% for endocrine therapy combined with abemaciclib), whereas the PALLAS trial has not found apparent benefit of the strategy. The NATALEE trial has not been reported yet.

Zembutsu et al. disclose that genetic variation in CYP2D6 is a key predictor for the response to tamoxifen in patients with breast cancer (Clin Cancer Res 2017; 23:2019-2026).

At present, there is no way of determining if a patient with early hormone-positive breast cancer could benefit from endocrine therapy alone and obtain a similar benefit to that observed from the combination with CDK4/6 inhibitors. Thus, there is a need for an easy test to help discern which patients need the combination of the endocrine therapy with CDK4/6 inhibitors from those who would already benefit from the endocrine therapy alone.

SUMMARY OF THE INVENTION

In a first aspect, the present invention relates to a method of determining the therapy for treating a subject afflicted from breast cancer comprising: (a) determining the P27 T2871099G SNP in a sample of said subject; and (b) administering only endocrine therapy if the polymorphism is other than T2871099G, and administering endocrine therapy in combination with at least one CDK4/6 inhibitor if the polymorphism is homozygous T2871099G.

In a second aspect, the present invention relates to a kit of parts for determining the treatment of a subject afflicted from breast cancer to be endocrine therapy alone or endocrine therapy in combination with at least one CDK4/6 inhibitor, consisting of means for determining, for the two copies of the p27 gene present in the subject, the identity of the nucleotide at the polymorphic site P27 T2871099G.

In a third aspect, the present invention relates to the use of the kit of parts of the second aspect for determining the treatment of a subject afflicted from breast cancer to be endocrine therapy alone or endocrine therapy in combination with at least one CDK4/6 inhibitor, preferably in a subject afflicted from early hormone-positive breast cancer.

DESCRIPTION OF THE INVENTION

Figure 1:
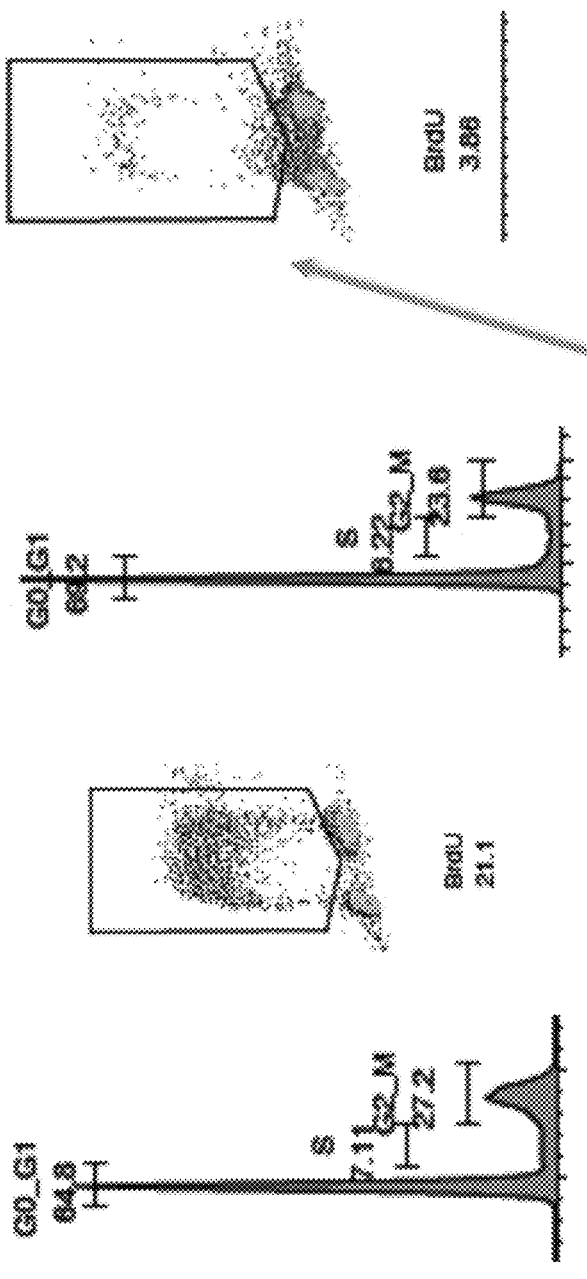
FIG. 1: Cell cycle with hormonal blockade in wild p27 background: behaviour of wild-type T47 cells. When comparing the left graph (vehicle) and the right graph (aromatase inhibition), it is observed that cell cycle is arrested with hormonal blockade.

Currently, there are not any available methods to discern which patients are sufficiently well treated with endocrine therapy from those that require combination with CDK inhibitors. However, with the detection of the polymorphism of the present invention (P27 T2871099G SNP), the difference in the benefit of the endocrine therapy for the patients is of six times, much bigger than with the genetic variation disclosed by Zembutsu et al. mentioned before.

The inventors have found that patients that harbour the T2871099G SNP in P27$^{kip}$ are refractory to hormonal blockade; however, the effect is abrogated by adding a CDK4/6 inhibitor. In advanced disease, patients that are homozygous for the SNP, when they receive aromatase inhibitors alone, their progression-free survival is just 3 months (3 to 4-fold lower than the average population when exposed to aromatase inhibitors alone). When treated with an aromatase inhibitor plus a CDK4/6 inhibitor, the phenotype is rescued and patients homozygous for the SNP show similar progression-free survival time to that of wild-type or heterozygous patients. These results would justify genomic testing in advanced disease for selection for treatment with CDK4/6 inhibitors or hormonal therapy alone. The inventors have shown that patients that do not harbour the SNP and receive hormonal monotherapy achieve a disease control duration in the first line of approximately 750 days (2 years); however, when the patients have a polymorphic genotype the disease control with hormones lasts only 120 days. Fortunately, polymorphic patients that receive also a CDK inhibitor have a disease control similar to the wild-type patients. Adding a CDK inhibitor in the first line in wild-type patients does not seem to confer a great benefit, according to the inventors data. Thus, patients could be stratified to receive only hormonal therapy or combination therapy according to their genotype.

The inventors have found that the P27 T2871099G SNP, easy to determine quickly, robustly and in an inexpensive manner, splits hormone-positive breast cancer patients in two groups. The first group comprises patients wild-type (approximately 45%) and patients heterozygous for the SNP (approximately 45%), and the second group comprises patients who are homozygous for this SNP (approximately 10%). When the patients have hormone-positive advanced breast cancer, the first group has around 10 months benefit from endocrine therapy, while the second group has around 3 months benefit from endocrine therapy. However, the benefit when endocrine therapy is combined with CDK4/6 inhibitors in patients with advanced breast cancer is the same in both groups. This means that the second group, bearing the SNP in homozygosis, needs the combined therapy to benefit from the endocrine therapy.

Moreover, in early disease, most of the patients would be adequately treated with endocrine therapy only but around 10% of them having the SNP in homozygosis would need the combined therapy with a CDK4/6 inhibitor.

At present, in the absence of this marker, the combined therapy is administered to all patients with early hormone-positive breast cancer, while only around 10% benefits from it.

The genotyping is a very simple test, that can be done in less than a day, with a close to 100% accuracy by different PCR modalities being the cost per determination very low. Genotyping by PCR is robust and simple, and a close to 100% inter-operator or inter-site concordance is expected.

P27 T2871099G SNP is the first useful biomarker for stratifying patients for treatment with endocrine therapy alone or combination therapy. The current solution is "playing it safe" and giving the combo to everybody, but this may result in an unbearable healthcare cost, unnecessary cases of acquired resistance to CDK inhibitors in wild type patients, and unnecessary toxicity. This biomarker solves all those issues, while maintaining the currently accepted as standard disease control duration for the combo. All patients diagnosed of hormone-positive breast cancer amenable of treatment with CDK inhibitors should be tested. This represents a population greater than 100,000 patients per year.

Besides, in the Western world, there are more than 600,000 patients with early hormonal breast cancer each year who could benefit from treatment with CDK inhibitors instead of hormone therapy alone if they have the P27 T2871099G polymorphism, which can be analysed very simply, reliably and quickly in a patient sample, such as a blood sample.

As used herein, the expression "single-nucleotide polymorphism" refers to a variation at a single position in a DNA sequence among individuals. If more than 1% of a population does not carry the same nucleotide at a specific position in the DNA sequence, then this variation can be classified as a SNP. SNPs can impact on mRNA splicing, nucleo-cytoplasmic export, stability, and translation. When present within a coding sequence and leading to an amino acid change, they can modify the protein's activity. The SNP of the present invention can be referred to as P27 T2871099G or CDKN1Brs2871099T:G or CDKN1B 2871099T:G or rs2066827 or T2871099G or V109G polymorphism or simply as SNP, indistinctively. Gene p27 is also known as Kip1, CDKN1B (cyclin dependent kinase inhibitor 1B), p27$^{kip}$, CDKN4, MEN1B, MEN4, or P27KIP1, and its sequence is in NCBI Reference Sequence: NG_016341 (version 1).

The terms "wild-type" or "WT" as used herein refer to the patient or cell line being homozygous and having the nucleotide T at the SNP of the invention, i.e.: having nucleotide T in both chromosomes at the SNP position.

The terms "heterozygous" or "hetero" as used herein refer to the patient or cell line being heterozygous for the SNP of the invention, i.e.: having nucleotide T in one chromosome and nucleotide G in the other, at the SNP position.

The terms "homozygous T2871099G", "SNP homozygous", "Homo SNP", "homozygous for the (T2871099G) SNP in P27$^{kip}$" or simply "homozygous" as used herein refer to the patient or cell line being homozygous and having the nucleotide G at the SNP of the invention, i.e.: having nucleotide G in both chromosomes at the SNP position.

In a preferred embodiment, the breast cancer is hormone-positive breast cancer. As used herein, the term hormone-positive breast cancer refers to hormone receptor-positive breast cancer, where cells have either estrogen (ER) or progesterone (PR) receptors or both.

In a preferred embodiment, the breast cancer is advanced breast cancer or early breast cancer, preferably is early breast cancer. In a preferred embodiment, the breast cancer is early hormone-positive breast cancer. As used herein, the expression "advanced breast cancer" includes stage 3 and stage 4 breast cancer. Metastatic or stage 4 breast cancer is cancer that has spread to other parts of the body. Locally advanced or stage 3 breast cancer has all the characteristics of advanced breast cancer but without affecting far-away organs. As used herein, the expression "early breast cancer" includes stage 1 and stage 2 breast cancer. Stage 1 and 2 breast cancer refers to invasive breast cancer that is contained within the breast and may or may not have spread to the lymph nodes in the armpit.

In a preferred embodiment, the sample is selected from the group consisting of plasma, serum, blood, saliva, skin, hair, tears, urine, fecal material, sweat, buccal smears, and a breast tissue biopsy. Preferably, the sample is a saliva or a blood sample.

In a preferred embodiment, the P27 T2871099G SNP is determined in step (a) using sequencing, PCR, RT-PCT, PCR and restriction enzyme, PCR and sequencing or next generation sequencing. Preferably, it is determined by RT-PCT. Preferably, it is determined by PCT followed by sequencing.

When the P27 T2871099G SNP is determined by PCR and restriction enzyme, the SNP region is first amplified by PCR and then the amplified region is treated with a restriction enzyme which activity depends on the P27 T2871099G SNP. Thus, the result of the treatment with the restriction enzyme allows the determination of the P27 T2871099G SNP.

In a preferred embodiment, the endocrine therapy consists of at least one aromatase inhibitor, preferably letrozole, and/or at least one estrogen inhibitor, preferably tamoxifen. As used herein, the terms "endocrine therapy", "hormonal blockade", "hormonal therapy", "hormone therapy" or "hormonal monotherapy" refer to drugs that stop the hormones from attaching to the receptors on the cancer cells, such as tamoxifen, toremifene, fulvestrant, or to drugs that stop the body from making estrogen after menopause, such as aromatase inhibitors (anastrozole, exemestane, letrozole). For women who have not undergone menopause (either naturally or as a result of cancer treatment), there is the option of stopping their ovaries from producing hormones by surgery to remove the ovaries (oophorectomy), radiation therapy aimed at the ovaries, or medications, such as goserelin. Treatments to stop ovarian function may allow premenopausal women to take medications only available to postmenopausal women (aromatase inhibitors). As used herein, the expression "aromatase inhibitors" refers to compounds that inhibits the enzyme aromatase and lower the level of the estrogen or estradiol. As used herein, the expression "estrogen inhibitors" refers to estrogen receptor antagonists.

As used herein, "combined therapy", "combo" or "combination therapy" refer to combining endocrine therapy with targeted therapies such as abemaciclib, palbociclib, ribociclib, trilaciclib, dinaciclib or everolimus. Preferably, this combination is of the endocrine therapy with CDK4/6 inhibitors. Preferably, the CDK4/6 inhibitors are selected from palbociclib or ribociclib or abemaciclib or a combination thereof. As used herein, the term "CDK4/6 inhibitors" refers to Cyclin Dependent Kinase 4 and 6 inhibitors that induce cytostasis through cell-cycle arrest in the G1 phase, resulting in growth inhibition. Examples of CDK4/6 inhibitors are palbociclib, ribociclib, abemaciclib, trilaciclib and dinaciclib. Preferred CDK4/6 inhibitors are palbociclib, ribociclib and abemaciclib.

In a second aspect, the present invention relates to a kit of parts for determining the treatment of a subject afflicted from breast cancer to be endocrine therapy alone or endocrine therapy in combination with at least one CDK4/6 inhibitor, consisting of means for determining, for the two copies of the p27 gene present in the subject, the identity of the nucleotide at the polymorphic site P27 T2871099G. Preferably, the means for determining a genetic polymorphism at the p27 polymorphic site P27 T2871099G comprise means for determining a genetic polymorphism pattern at the p27 polymorphic site P27 T2871099G. Preferably, the means for determining a genetic polymorphism pattern at the p27 polymorphic site P27 T2871099G comprise at least one P27 T2871099G genotyping oligonucleotide. P27 T2871099G genotyping oligonucleotides of the invention may also be immobilized on or synthesized on a solid surface such as a microchip, bead or glass slide. Such immobilized genotyping oligonucleotides may be used in a variety of polymorphism detection assays, including but not limited to probe hybridization and polymerase extension assays. Immobilized P27 T2871099G genotyping oligonucleotides of the invention may comprise an ordered array of oligonucleotides designed to rapidly screen a DNA sample for polymorphisms in multiple genes at the same time. Other genotyping oligonucleotides of the invention hybridize to a target region located one to several nucleotides downstream of one of the novel polymorphic sites identified herein. Such oligonucleotides are useful in polymerase-mediated primer extension methods for detecting one of the novel polymorphisms described herein and therefore such genotyping oligonucleotides are referred to herein as "primer-extension oligonucleotides". In a preferred embodiment, the 3'-terminus of a primer-extension oligonucleotide is a deoxynucleotide complementary to the nucleotide located immediately adjacent to the polymorphic site.

The target region may be amplified using any oligonucleotide-directed amplification method, including but not limited to polymerase chain reaction (PCR), ligase chain reaction (LCR), and oligonucleotide ligation assay (OLA). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan. Other known nucleic acid amplification procedures may be used to amplify the target region including transcription-based amplification systems and isothermal methods. A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs. Preferably, the members of the set have melting temperatures within 5° C. and more preferably within 2° C., of each other when hybridizing to each of the polymorphic sites being detected. The genotype for the P27 T2871099G SNP of a subject may also be determined by hybridization of a nucleic sample containing one or both copies of the gene to nucleic acid arrays and subarrays.

In another embodiment, the invention provides a kit comprising at least two genotyping oligonucleotides packaged in separate containers. The kit may also contain other components such as hybridization buffer (where the oligonucleotides are to be used as a probe) packaged in a separate container. Alternatively, where the oligonucleotides are to be used to amplify a target region, the kit may contain, packaged in separate containers, a polymerase and a reaction buffer optimized for primer extension mediated by the polymerase, such as PCR.

More preferably, the means for determining a genetic polymorphism pattern at the p27 polymorphic site P27 T2871099G comprise two genotyping oligonucleotides. Preferably, the means for determining a genetic polymorphism pattern at the p27 polymorphic site P27 T2871099G comprise at least one p27 genotyping primer composition comprising at least one p27 genotyping oligonucleotide, preferably comprising at least two sets of allele specific primer pairs, more preferably wherein the two p27 genotyping oligonucleotides are packaged in separate containers.

In a preferred embodiment, the means for determining a genetic polymorphism pattern at the p27 polymorphic site P27 T2871099G comprise DNA sample collecting means.

For example, the kit of parts may comprise as means for determining a genetic polymorphism at the p27 polymorphic site P27 T2871099G, primers SEQ ID NO: 1, SEQ ID NO: 2, SEQ ID NO: 3, SEQ ID NO: 4, SEQ ID NO: 5, SEQ ID NO: 6, or any combination thereof. For example, SEQ ID NO: 1 and SEQ ID NO: 2 can be used for PCR and SEQ ID NO: 3 for sequencing the amplified region. Also, SEQ ID NO: 1 and SEQ ID NO: 4 can be used for PCR and SEQ ID NO: 3 for sequencing the amplified region. Primers SEQ ID NO: 5 and SEQ ID NO: 4 can also be used for PCR, and SEQ ID NO: 6, SEQ ID NO: 2 or SEQ ID NO: 4 can be used interchangeably for sequencing.

A third aspect of the present invention relates to the use of the kit of parts of the second aspect for determining the treatment of a subject afflicted from breast cancer to be endocrine therapy alone or endocrine therapy in combination with at least one CDK4/6 inhibitor, preferably in a subject afflicted from early hormone-positive breast cancer.

Another aspect of the present invention relates to a method for predicting the response to hormone therapy in breast cancer comprising the determination of the P27 T2871099G single-nucleotide polymorphism (SNP) in a sample of a subject afflicted from breast cancer. If the P27 T2871099G single-nucleotide polymorphism is found in homozygosis, it can be predicted that the response to the combined therapy will be better than endocrine therapy alone.

Another aspect of the present invention refers to a method for treating a subject having breast cancer comprising determining the P27 T2871099G SNP and administering only hormone therapy if the polymorphism is other than T2871099G and administering hormonal therapy in combination with CDK4/6 inhibitors if the polymorphism is homozygous T2871099G. Preferably, the breast cancer is hormone-positive breast cancer, more preferably, early hormone-positive breast cancer. Preferably, the CDK4/6 inhibitor compound is selected from palbociclib or ribociclib or abemaciclib or a combination thereof. Preferably, the hormone therapy is at least one aromatase inhibitor, preferably letrozole, and/or at least one estrogen inhibitor, preferably tamoxifen.

EXAMPLES

Example 1: Patients Homozygous for T2871099G SNP and Advanced Hormone-Positive Breast Cancer are Refractory to Hormonal Treatment but are Rescued with CDK4/6 Inhibitors The inventors gathered a series of 106 advanced breast cancer patients of the hormone positive subtype; their distribution according to the treatment line is shown below in Table 1.

TABLE 1 distribution of patients according to their treatment.

| Line | Number of patients | Genotype: number of patients |
|---|---|---|
| First line, Hormonal blockade only | 32 | Wild-type: 15 (48%) Hetero: 13 (42%) Homo SNP: 4 (13%) |
| First line, Hormonal + CDK blockade | 26 | Wild-type: 10 (38%) Hetero: 12 (46%) Homo SNP: 4 (15%) |
| Other lines | 48 | Similar |

The inventors then compared the progression-free survival of patients homozygous for the (T2871099G) SNP in P27$^{kip}$ with a group constituted by Wild-type and heterozygous patients receiving hormonal therapy alone. The median progression-free survival for the homozygous patients was 92 days, compared to 548 days in the remaining patients (P<0.0001). Thus, homozygous patients do not derive benefit from hormonal blockade alone.

In patients with advanced, hormone-positive breast cancer, treated with the combination of hormonal blockade plus CDK4/6 inhibitor in the first line, when the CDK4/6 inhibitor is added, the negative effect is rescued: homozygous patients showed a median progression-free survival of 658 days, compared to 501 days for the group of heterozygous plus wild-type patients (P: non-significant).

In can be concluded that, in first-line metastatic hormone-positive breast cancer, the (T2871099G) SNP in P27$^{kip}$ is a biomarker for therapeutic selection: Homozygous patients would require double aromatase and CDK4/6 inhibitors, whereas wild-type or heterozygous patients would be adequately treated with endocrine therapy.

Example 2: Generation of Isogenic Hormone-Positive Breast Cancer Cell Lines Wild-Type or Polymorphic for T2871099G SNP From a panel of 14 breast cancer cell lines, the inventors selected those that were wild-type for both alleles of the P27 gene (T47, JIMT-1, BT474, MDA-MB-415 and EVSA-T). Then, taking advantage of CRISPR technology, they substituted the base pair causing the amino-acid change of interest, generating both heterozygous and homozygous variants.

TABLE 2

Panel of 14 breast cancer cell lines.

| | T/T | T/G | G/G |
|---|---|---|---|
| MCF7 | | ✓ | |
| HCC1428 | | ✓ | |

TABLE 2-continued

| | T/T | T/G | G/G |
|---|---|---|---|
| Panel of 14 breast cancer cell lines. | | | |
| T47D | ✓ | | |
| ZR75-1 | | ✓ | |
| CAMA-1 | | ✓ | |
| BT483 | | ✓ | |
| MDA-MB175VII | | ✓ | |
| JIMT-1 | ✓ | | |
| KPL-1 | | ✓ | |
| ZR75-30 | | | |
| BT474 | ✓ | | |
| SKBR-3 | | ✓ | |
| MDA-MB415 | ✓ | | |
| EVSA-T | ✓ | | |

Example 3: Effects of the T2871099G SNP in Cell Cycle and RB

The inventors next compared the effects of the T2871099G SNP in the cell cycle. To that end, they compared the BrdU uptake of wild-type of homozygous cells, treated with vehicle or with hormonal deprivation. FIG. 1 shows the behaviour of wild-type T47 cells. The cells highlighted in the square of FIG. 1 are those with active replication. It can be appreciated how the replicative fraction falls from 21% to just 3% when we apply hormonal deprivation to wild-type cells.

Figure 2:
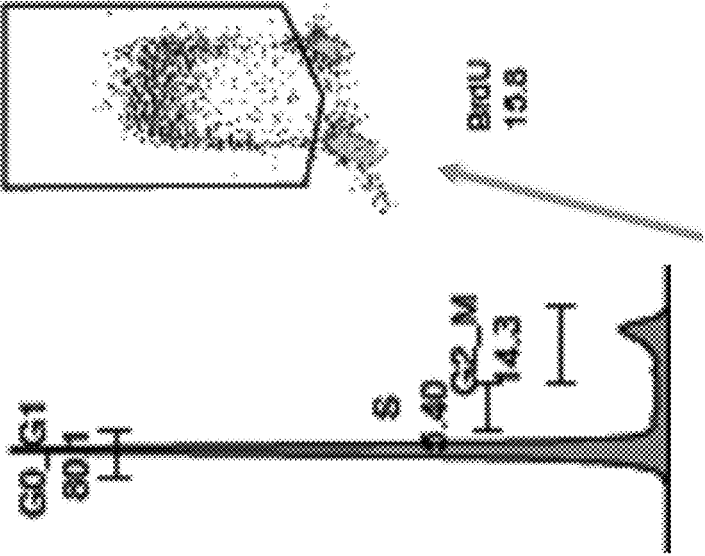
FIG. 2: The cell cycle is unaffected in cells homozygous for the SNP. When comparing the left graph (vehicle) and the right graph (aromatase inhibition), it is observed that the cell cycle is unaffected.
Figure 2:
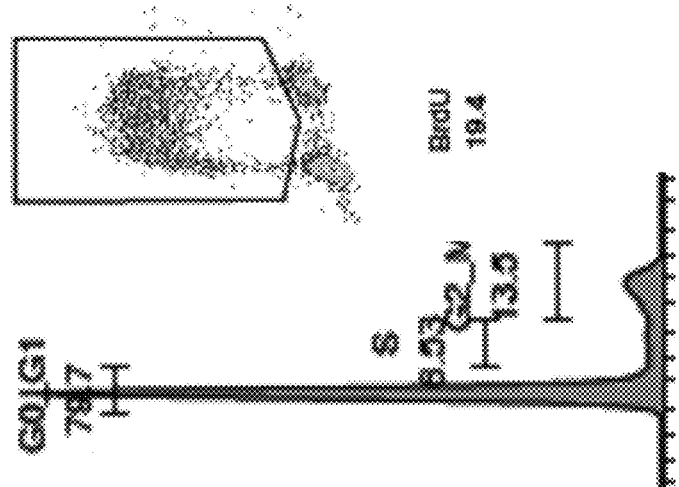

However, FIG. 2 illustrates how the cell cycle is unaffected in cells homozygous for the T2871099G SNP. As opposed to FIG. 1, here we can observe how the cell cycle is unaffected in response to hormonal deprivation.

Figure 3:
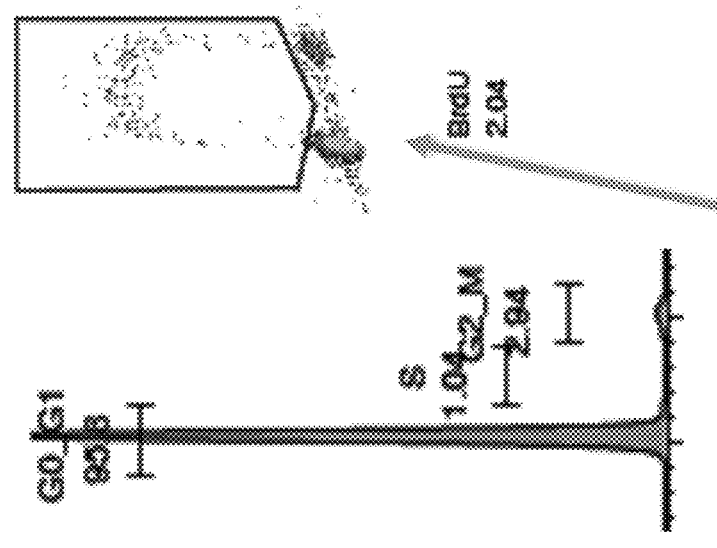
FIG. 3: Effects of double blockade (hormonal deprivation plus CDK4/6 inhibitor (palbociclib)) comparing wild-type T47D cells (left graph) and homozygous T47D cells (right graph). The cell cycle is fully suppressed despite the background.
Figure 3:
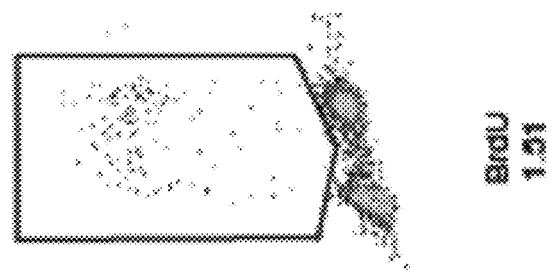
Figure 3:
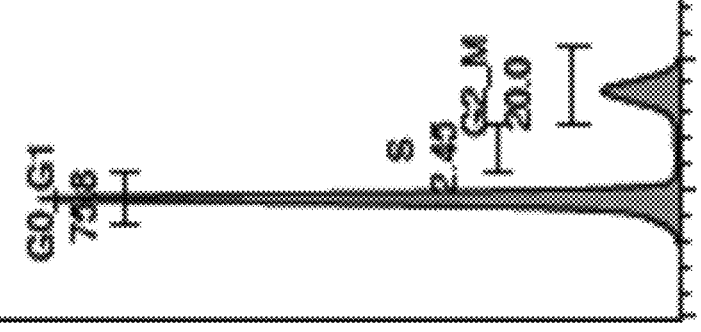

Finally, the inventors tested whether when they add palbociclib, a CDK4/6 inhibitor, the refractoriness was rescued or not. In FIG. 3 we can observe the effects of double blockade (hormonal deprivation plus CDK4/6i) comparing wild-type and homozygous cells. As it can be observed, wild-type and homozygous cells respond similarly to the double blockade, leading to a near-complete arrest of cell cycle.

The activity of Rb is to restrain cells from entering the cell cycle. Cyclin D/CDK4 complexes phosphorylate Rb, what leads to its degradation (inactivation), allowing the entrance in the cell cycle. Blocking Cyclin D/CDK4 complexes leads to an impaired kinase activity and stability of Rb. The inventors have applied 4 different treatments: FBS (full medium, no drugs), DCC (hormonal deprivation), DCC+P (hormonal deprivation plus CDK4/6 blockade with palbociclib) and Palbo (palbociclib alone). In each condition, a pair of cell lines are presented: wild-type T47-D and homozygous for the T2871099G SNP (clone C1). It can be observed that Rb is always more phosphorylated in C1 than in the parental cells, unless Palbociclib is added. In conclusion, the cell cycle is active even in presence of hormonal blockade when the T2871099G SNP exists, and full cell cycle arrest occurs only when CDK4/6 is blocked.

Example 4: Potential Mechanism of Resistance to Hormonal Therapy and Requirement of CDK4/6 Blockade As mentioned before, the entrance of the cell in active cycling is controlled by the Cyclin D/CDK 4 complexes. The cell cycle is also controlled by the Cyclin A/CDK2 complexes. The inventors performed co-immunoprecipitation assays. These assays allow detecting the proteins that partner-up with a protein of interest. Here, they compared whether Cyclin D and CDK4/6, or Cyclin A and CDK2, were together or not and to what extent in wild-type of polymorphic cell variants. They compared several conditions: untreated, treated with hormonal deprivation alone, treated with hormonal deprivation and Palbociclib, and treated with Palbociclib alone. Pulling-down CDK4 and blotting for Cyclin D allows answering the question of how much Cyclin D was bound to CDK4 in different conditions (untreated, hormonal blockade, hormonal blockade plus Palbociclib, or Palbociclib alone) between wild-type and the F5 homozygous clone. It was found that the amount of bound Cyclin D1 is higher in untreated cells and cells treated with hormonal blockade alone in F5 clone, but it only gets back to normal (i.e., same levels as in parental cells) when treated with hormonal blockade plus Palbociclib. Similarly, the amount of Cyclin A bound to CDK2 only decreases back to normal (i.e., akin wild-type cells) in the hormonal blockade plus Palbociclib condition. This means that in baseline conditions, the amount of complexes that fire the cell cycle is always higher in cells with the polymorphic variant, and hormonal blockade is unable to disrupt those clones. However, Palbociclib treatment is able to do so. P27, in wild-type conditions, is known to restrain the formation of these complexes. We believe that the amino acid substitution impairs P27 function, and thus the cell cycle is unrestrained in polymorphic cells. This modification is refractory to hormonal changes. However, since Palbociclib works downstream of this step, the combination of hormonal blockade plus Palbociclib is able to rescue the deficit in cell cycle control, achieving complete cell cycle arrest.

In summary, the wild-type allele is able to arrest cell cycle, even more when hormonal signals are lacking (hormonal treatment). This physiological property is lost in presence of the variant allele, allowing too many CDK2/Cyclin A and CDK4/Cyclin D complexes to form and pair-up, which phosphorylate and inactivate Rb, leading to unrestrained cell cycle and failure to hormonal treatment. Treatment with CDK 4/6 inhibitors resolves this phenotype.

Finally, the inventors exposed a wild-type and a polymorphic cell line to permanent hormonal deprivation. This approach usually causes most cells to die after 4-6 days, but, if the cell culture is left untouched, and media is replaced, in about two years, a few clones emerge and show long-term estrogen-deprivation resistant phenotype. The inventors have repeated this process with several wild-type cell lines (T47D, MCF-7, HCC1428, EVSAT) and it always takes more than 2 years. However, the polymorphic cell line is able to acquire this phenotype in 8 to 12 months, displaying a similar phenotype to that of patients—refractoriness to hormonal blockade. Therefore, the SNP in P27$^{kip}$ (T2871099G) that is present in homozygous state in approximately 10% of breast cancer patients, leads to refractoriness to hormonal blockade and this defect, however, is rescued by treatment with CDK4/6 inhibitors. Also, wild-type P27$^{kip}$ is able to restrain the formation of cell cycle activating complexes: CDK2/cyclin A and CDK4/cyclin D. However, the polymorphic variant is not, even in presence of hormonal blockade. Furthermore CDK4/6 inhibitors are able to restore cell cycle arrest in the former condition, disrupting the complexes, that such disruption leads to normalization of Rb phosphorylation levels and treatment sensitivity and that the SNP in P27$^{kip}$ (T2871099G) can be used as a treatment selection factor: wild-type patients would be adequately treated with endocrine therapy alone, while homozygous patients would require treatment with hormonal blockade combined with CDK4/6 inhibitors.

METHODS

Patient Genotyping for P27 kip1 Variants

Blood sample for each patient was obtained by standard procedures during routine doctor visit at hospital. DNA extraction, was performed using DNeasy Blood and Tissue kit (#69504, Qiagen) following manufacturer instructions. In order to evaluate the presence of V109G polymorphism on p27 Kip1 gene, a first PCR from 200 ng of DNA was done using Platinum PCR Supermix (#11306-016, Invitrogen) and the primers: FW 5' GTCAAACGTGCGAGTGTCTAAC 3' (SEQ ID NO: 1) and REV 5' CAGACAAGCAGTGGGCCAGG3' (SEQ ID NO: 2) flanking the codon of interest. PCR product was verified by running 5 ul of PCR reaction on an agarose gel; the rest of reaction was purified using QIAquick PCR purification kit (#28106, Qiagen) following manufacturer instructions and sequenced by Sanger methodology using an internal primer (5' CTTGGAGAAGCACTGCAGAGA-CATG 3', SEQ ID NO: 3). The PCR can also be performed with primers SEQ ID NO: 1 and REV 5' CATCC-CAACTTTGTCACATACCTAG 3' (SEQ ID NO: 4), as well as with FW 5'GTGCAGACCCGGGAGAAAGATGT 3' (SEQ ID NO: 5) and REV SEQ ID NO: 2 or SEQ ID NO: 4. The sequencing can also be performed with primers 5' GAGGTGGAGAAGGGCAGC 3' (SEQ ID NO: 6), SEQ ID NO: 2, or SEQ ID NO: 4.

Generation of a Stable Cell Line Expressing V109G Polymorphism by Edit-R CRISPR-Cas9 Technology DNA from 14 cell lines (MCF7, HCC1428, T47D, ZR75-1, CAMA-1, BT483, MDA-MB175VII, JIMT-1, KPL-1, ZR75-30, BT474, SKBR-3, MDA-MB-415 and EVSA-T) were screened for detection of V109G polymorphism in p27 Kip1 gene by the procedures described above for patients. None of the cell lines showed the homozygous sequence for the polymorphism. T47D and EVSA-T were homozygous for the wild type allele, so we decided to use the Edit-R CRISPR-Cas9 genome engineering technology to introduce the mutated allele following manufacturer instructions (IDT Integrated DNA Technology). Briefly, cells were electroporated with Cas9:crRNA:tracrRNAribonucleoprotein (RNP) complex using Neon transfection system. After two days, cells were sorted into 96-well plates for single cell isolation (Influx cell sorter), and kept in culture until individual clones were observed. These clones were grown into 6-well plates and in order to verify the edition of the genome, DNA from each clone were first analysed by PCR-based detection (RFLP) method and finally the confirmation of the genotype by Sanger sequencing as previously described. We obtained 4 clones with the homozygous mutation for T47D cell line (clone A10, C1, E1 and F5) and 3 clones for EVSAT cell line (clone C7, G10 and H6).

Generation of Hormone-Resistant Clones

T47D wt cell line and the different clones (clone A10, C1, E1 and F5) were maintained following the ATCC recommendations and routinely tested for *mycoplasma* using the Mycoalert™ Mycoplasma Detection Kit (Lonza). Cell line clones resistant to estrogen deprivation were generated following the method consisted of weekly passage and culture of cells in medium containing 10% dextran charcoal-stripped (DCC) fetal bovine serum (FBS) (Sigma) instead of full FBS, which removes steroids. The medium was changed every 2-3 days for 2 years until acquisition of the LTED-R phenotype. This process usually lasts more than a year.

Colony-Formation Assays

Colony-formation assays were conducted as follows: breast cancer cell lines were seeded at densities of 2000 (T47D wt or clones A10, C1, E1 and F5) and 1000 (EVSAT wt or clones C7, G10 and H6) cells per well in 12-well plates. After overnight incubation, medium was replaced with fresh medium with either vehicle (control), drugs (fulvestrant and palbociclib) or cells were grown in medium containing 10% dextran charcoal-stripped (DCC) fetal bovine serum (FBS). Media and drugs were refreshed every 3-4 days. After 10 days of culture, cells were fixed and stained with 0.1% (w/v) crystal violet in 10% (v/v) ethanol. All experiments were performed at least in triplicate. The well area covered by colonies (colony area intensity) was quantified automatically from flatbed scanner-acquired images of colony assays conducted in multi-well plates using the ImageJ software.

Cell Cycle Assays

Regarding cell-cycle assays, cells were pre-treated with drugs or vehicle for 48 h and then 10 μM BrdU was added to the medium for 30 min before harvesting. Fixed cells were treated with 2 M HCl for 20 min, and BrdU was immunolabeled with FITC-conjugated anti-BrdU (Cat. 556028, BD Pharmigen™). For DNA-content analysis, cells were fixed in 70% ethanol, washed in PBS and stained with 50 μg/ml propidium iodide (Sigma) in the presence of 10 μg/ml RNase A (Qiagen). Flow cytometry data were acquired in a FACSCanto cytometer (BD Biosciences) and analyzed with FlowJo software (Tree Star Inc.).

Co-Immunoprecipitation

For the immunoprecipitation studies, whole-cell lysates were prepared in RIPA lysis buffer (Sigma) containing 1% Halt™ Protease & Phosphatase inhibitor cocktail, EDTA-free (Thermo Scientific #78441). Target antibodies and control isotypes IgGs were firstly incubated with protein lysates for an hour on rotation at 4° C. Then, protein A/G Plus agarose beads (Santa Cruz, #sc-2003) were added and the mix were incubated in rotation overnight at 4° C. For western blotting agarose beads were washed three times with lysis buffer and then boiled in presence of Laemmli buffer (1×). The following antibodies were used for immunoprecipitations: p27 Kip1 (D69C12) (#3686 Cell Signaling), CDK2 (#A301-812A, Bethyl), CDK4 (DCS-35) (MA5-12984, Invitrogen), CDK6 (D4S8S) (#1331, Cell Signaling), Cyclin A (B-8) (#sc-271682, Santa Cruz), Cyclin D1 (E3P5S) (#55506, Cell Signaling) and Cyclin E1 (E4) (#sc-377100, Santa Cruz). The following antibodies were used for immunoblotting: p27 Kip1 (F8) (#sc-1641, Santa Cruz), CDK4 (D9G3E) (#12790, Cell Signaling), Cyclin A (#sc-571, Santa Cruz) and Cyclin E1 (D7T3U) (#20808, Cell Signaling).

The invention claimed is:

1. A method of determining the therapy for treating a subject afflicted from breast cancer comprising:
   a. determining the P27 T2871099G SNP in a sample of said subject, and then
   b. administering only endocrine therapy if the polymorphism is other than T2871099G, and administering endocrine therapy in combination with at least one CDK4/6 inhibitor if the polymorphism is homozygous T2871099G.

2. The method of the preceding claim, wherein the breast cancer is hormone-positive breast cancer.

3. The method of claim 1, wherein the breast cancer is advanced breast cancer or early breast cancer.

4. The method of claim 1, wherein the sample is selected from the group consisting of plasma, serum, blood, saliva, skin, hair, tears, urine, fecal material, sweat, buccal smears, and a breast tissue biopsy.

5. The method of claim 1, wherein the P27 T2871099G SNP is determined in step (a) using sequencing, PCR, RT-PCR, PCR and restriction enzyme, PCR and sequencing or next generation sequencing.

6. The method of claim 1, wherein the endocrine therapy consists of at least one aromatase inhibitor, and/or at least one estrogen inhibitor.

7. The method of claim 1, wherein CDK4/6 inhibitor is selected from palbociclib or ribociclib or abemaciclib or a combination thereof.

8. The method of claim 3, wherein the breast cancer is early breast cancer.

9. The method of claim 4, wherein the sample is saliva or blood.

10. The method of claim 6, wherein the aromatase inhibitor is letrozole and the estrogen inhibitor is tamoxifen.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Homo sapiens

<400> SEQUENCE: 1
gtcaaacgtg cgagtgtcta ac                                          22

<210> SEQ ID NO 2
<211> LENGTH: 20
<212> TYPE: DNA
<213> ORGANISM: Homo sapiens

<400> SEQUENCE: 2
cagacaagca gtgggccagg                                             20

<210> SEQ ID NO 3
<211> LENGTH: 25
<212> TYPE: DNA
<213> ORGANISM: Homo sapiens

<400> SEQUENCE: 3
cttggagaag cactgcagag acatg                                       25

<210> SEQ ID NO 4
<211> LENGTH: 25
<212> TYPE: DNA
<213> ORGANISM: Homo sapiens

<400> SEQUENCE: 4
catcccaact ttgtcacata cctag                                       25

<210> SEQ ID NO 5
<211> LENGTH: 23
<212> TYPE: DNA
<213> ORGANISM: Homo sapiens

<400> SEQUENCE: 5
gtgcagaccc gggagaaaga tgt                                         23

<210> SEQ ID NO 6
<211> LENGTH: 18
<212> TYPE: DNA
<213> ORGANISM: Homo sapiens

<400> SEQUENCE: 6
gaggtggaga agggcagc                                               18
```